(12) United States Patent
Cesati et al.

(10) Patent No.: US 10,568,978 B2
(45) Date of Patent: Feb. 25, 2020

(54) RADIOPHARMACEUTICAL SYNTHESIS METHODS

(71) Applicant: Lantheus Medical Imaging, Inc., North Billerica, MA (US)

(72) Inventors: Richard R. Cesati, Pepperell, MA (US); James F. Castner, Groton, MA (US)

(73) Assignee: Lantheus Medical Imaging, Inc., North Billerica, MA (US)

(*) Notice: Subject to any disclaimer, the term of this patent is extended or adjusted under 35 U.S.C. 154(b) by 0 days.

(21) Appl. No.: 14/390,425

(22) PCT Filed: Apr. 10, 2013

(86) PCT No.: PCT/US2013/036027
§ 371 (c)(1),
(2) Date: Oct. 3, 2014

(87) PCT Pub. No.: WO2013/173004
PCT Pub. Date: Nov. 21, 2013

(65) Prior Publication Data
US 2015/0056136 A1     Feb. 26, 2015

Related U.S. Application Data (60) Provisional application No. 61/785,623, filed on Mar. 14, 2013, provisional application No. 61/622,515, filed on Apr. 10, 2012.

(51) Int. Cl.
| | |
|---|---|
| *A61K 51/00* | (2006.01) |
| *A61M 36/14* | (2006.01) |
| *A61K 51/12* | (2006.01) |
| *A61K 51/04* | (2006.01) |

(52) U.S. Cl.
CPC ........ *A61K 51/121* (2013.01); *A61K 51/0402* (2013.01); *A61K 51/0406* (2013.01); *A61K 51/0453* (2013.01); *A61K 51/0455* (2013.01); *A61K 51/0459* (2013.01); *A61K 51/0491* (2013.01)

(58) Field of Classification Search
CPC .. A61K 51/121; A61K 51/0459; A61K 51/04; C07B 59/00
USPC ....................................................... 424/1.73
See application file for complete search history.

(56) References Cited

U.S. PATENT DOCUMENTS

| | | | |
|---|---|---|---|
| 7,807,135 B2 | 10/2010 | Kung et al. | |
| 8,226,929 B2 | 7/2012 | Casebier et al. | |
| 8,491,868 B2 | 7/2013 | Purohit et al. | |
| 8,936,777 B2 | 1/2015 | Cesati et al. | |
| 2010/0266500 A1 | 10/2010 | Kung et al. | |
| 2011/0008254 A1 | 1/2011 | Roed et al. | |
| 2011/0091374 A1 | 4/2011 | Robinson et al. | |
| 2013/0149244 A1 | 6/2013 | Purohit et al. | |
| 2014/0328756 A1 | 11/2014 | Cesati et al. | |
| 2015/0196672 A1 | 7/2015 | Cesati et al. | |

FOREIGN PATENT DOCUMENTS

| | | |
|---|---|---|
| EP | 2 110 367 A1 | 10/2009 |
| WO | WO 2009/127372 A1 | 10/2009 |
| WO | WO 2010/060694 A1 | 6/2010 |
| WO | WO 2010120368 A2 * | 10/2010 |
| WO | WO 2011/006610 A1 | 1/2011 |
| WO | WO 2011-076825 A1 | 6/2011 |
| WO | WO 2011-097649 A2 | 8/2011 |
| WO | WO 2012/021882 A2 | 2/2012 |
| WO | WO 2012/040138 A2 | 3/2012 |
| WO | WO 2012/175641 A1 | 12/2012 |

OTHER PUBLICATIONS

Nandy et al. J. Radioanal. Nucl. Chem. (2010) 283: 741-748.*
Kalen et al. App. Rad. Isot. 65 (2007) 696-700.*
Scott et al. App. Rad. Isot. 2009, 67, 88-94.*
Wild et al. Cacner Res. 2011, 1-10.*
Smith et al. J. Med. Chem. 2008, 51, 8057-8067.*
International Search Report and Written Opinion for PCT/US2013/036027 dated Nov. 26, 2013.
International Preliminary Report on Patentability for PCT/US2013/036027 dated Oct. 23, 2014.
Lister-James et al., Florbetapir f-18: a histopathologically validated Beta-amyloid positron emission tomography imaging agent. Semin Nucl Med. Jul. 2011;41(4):300-4. doi:10.1053/j.semnuclmed.2011.03.001.
EP13790824.0, Oct. 14, 2015, Extended European Search Report.
Extended European Search Report for EP13790824.0 dated Oct. 14, 2015.

\* cited by examiner

*Primary Examiner* — Michael G. Hartley
*Assistant Examiner* — Sean R Donohue
(74) *Attorney, Agent, or Firm* — Wolf, Greenfield & Sacks, P.C.

(57) ABSTRACT

The invention relates to products and methods that provide increased yields of certain radiopharmaceuticals.

15 Claims, 9 Drawing Sheets

RADIOPHARMACEUTICAL SYNTHESIS METHODS

RELATED APPLICATIONS

This application is a national stage filing under 35 U.S.C. § 371 of International Application No. PCT/US2013/036027 filed on Apr. 10, 2013, which was published under PCT Article 21(2) in English, and which claims the benefit of U.S. Provisional Application Ser. No. 61/622,515 filed on Apr. 10, 2012, and U.S. Provisional Application Ser. No. 61/785,623 filed on Mar. 14, 2013, all entitled "RADIOPHARMACEUTICAL SYNTHESIS METHODS", the entire contents of each of which are incorporated by reference in their entirety herein.

SUMMARY OF INVENTION

The invention is based on the unexpected finding that increased yields of certain radiopharmaceuticals can be achieved when particular filters are used to sterilize solutions comprising the radiopharmaceuticals. The filters are typically used in a final sterilization step following synthesis however it is to be understood that the invention is not so limited and the filters may be used in any step during or post-synthesis. The increased yield achieved with particular filters, in accordance with the invention, relates to the differential retention properties of the various filters analyzed. It was not recognized nor was it expected prior to the invention that particular filters would demonstrate the varied retention profiles observed and documented herein. Moreover, it could not have been predicted which of the tested filters would be the best performing based on the various known properties of the various filters (e.g., hydrophobicity, etc.).

It was found in accordance with the invention that a filter comprised of regenerated cellulose (such as the Sartorius RC filter) and a filter comprised of polytetrafluoroethylene (such as the Millipore PTFE filter) were the best performing filters in terms of lowest retention of the filtered radiopharmaceutical. It is surprising that two such disparate filter types would nevertheless perform relatively equivalently and better than other filters that are more similar to one or the other of the RC or PTFE filters. As an example, a polyvinylidenedifluoride (PVDF) filter which is structurally more similar to PTFE than is RC nevertheless performed less well than did the RC filter in terms of reduced retention of the radiopharmaceutical. Also surprisingly, the matrix within which the radiopharmaceutical was provided was not changed, and it was able to tolerate different filters without compromise of radiopharmaceutical yield.

DETAILED DESCRIPTION OF INVENTION

The method of the invention may be used to sterilize a radiopharmaceutical, such as an $^{18}$F-bearing radiopharmaceutical (i.e., a composition intended for in vivo use, typically as an imaging agent, that comprises $^{18}$F). It is to be understood that the method may also be used to sterilize other radiopharmaceuticals. The method of the invention may also be used to simply physically separate a radiopharmaceutical from other agents including degradation products, contaminants, and the like, regardless of whether the ultimate filtered solution is considered sterile.

Examples of $^{18}$F-bearing radiopharmaceuticals include but are not limited to

[$^{18}$F]FLT (clogP = −0.41)

flurpiridaz F 18 (clogP = 3.04)

[$^{18}$F]β-CIT (clogP = 4.42)

Other examples include florbetapir, and florbetaben (disclosed in U.S. Pat. Nos. 7,687,052 and 7,807,135, respectively and shown below)

[$^{18}$F]florbetapir (clogP = 3.52)

[$^{18}$F]florbetaben (clogP = 4.12)

In some aspects of the invention, the radiopharmaceutical has a structure as in formula (I), (I)

wherein:

J is selected from N(R$^9$), S, O, C(=O), C(=O)O, NHCH$_2$CH$_2$O, a bond, or C(=O)N(R$^9$);

when present, K is selected from hydrogen, alkoxyalkyl, alkyloxy, aryl, C$_1$-C$_6$ alkyl, heteroaryl, and an imaging moiety;

when present, L is selected from hydrogen, alkoxyalkyl, alkyloxy, aryl, C$_1$-C$_6$ alkyl, heteroaryl, and an imaging moiety;

M is selected from hydrogen, alkoxyalkyl, alkyloxy, aryl, C$_1$-C$_6$ alkyl, heteroaryl, and an imaging moiety; or L and M, together with the atom to which they are attached, form a three-, four-, five-, or six-membered carbocyclic ring;

Q is halo or haloalkyl;

n is 0, 1, 2, or 3;

R$^1$, R$^2$, R$^7$, and R$^9$ are independently selected from hydrogen, C$_1$-C$_6$ alkyl, and an imaging moiety;

R$^3$, R$^4$, R$^5$, and R$^6$ are independently selected from hydrogen, halogen, hydroxyl, alkoxyalkyl, alkyloxy, C$_1$-C$_6$ alkyl, and an imaging moiety;

R$^8$ is C$_1$-C$_6$ alkyl; and

Y is selected from a bond, carbon, and oxygen; provided that when Y is a bond, K and L are absent and M is selected from aryl and heteroaryl; and provided that when Y is oxygen, K and L are absent and M is selected from hydrogen, alkoxyalkyl, aryl, C$_1$-C$_6$ alkyl, and heteroaryl;

wherein each occurrence of alkoxyalkyl, alkyloxy, aryl, C$_1$-C$_6$ alkyl, and heteroaryl is optionally substituted with an imaging moiety, provided that at least one imaging moiety is present in formula (I).

In some embodiments, J is O; M is selected from alkoxyalkyl, alkyloxy, aryl, C$_1$-C$_6$ alkyl, and heteroaryl, each optionally substituted with an imaging moiety; Q is halo or haloalkyl; n is 1; and R$^8$ is C$_1$-C$_6$ alkyl.

In some embodiments, J is O; M is alkyloxy substituted with an imaging moiety; Q is halo; n is 1; and R$_8$ is C$_1$-C$_6$ alkyl.

In some embodiments, J is O; and R$^8$ is tert-butyl. In some embodiments, Q is halo. In some embodiments, Q is chloro. In some embodiments, M is alkyloxy substituted with an imaging moiety.

In some embodiments, the imaging moiety is a radioisotope for use in nuclear medicine imaging, a paramagnetic species for use in MRI imaging, an echogenic entity for use in ultrasound imaging, a fluorescent entity for use in fluorescence imaging, or a light-active entity for use in optical imaging. In some embodiments, the paramagnetic species for use in MRI imaging is Gd$^{3+}$, Fe$^{3+}$, In$^{3+}$, or Mn$^{2+}$. In some embodiments, the echogenic entity for use in ultrasound imaging is a surfactant encapsulated fluorocarbon microsphere. In some embodiments, the radioisotope for use in nuclear medicine imaging is $^{11}$C, $^{13}$N, $^{18}$F, $^{123}$I, $^{125}$I, $^{99m}$Tc, $^{95}$Tc, $^{111}$In, $^{62}$Cu, $^{64}$Cu, $^{67}$Ga, or $^{68}$Ga. In some embodiments, the imaging moiety is $^{18}$F.

It is to be understood that radiopharmaceuticals include imaging agents. Thus, some embodiments of the invention are described in terms of imaging agents.

In some embodiments, the imaging agent is selected from the group consisting of

In one embodiment, a composition is provided comprising ascorbic acid and an imaging agent, wherein the imaging agent comprises pyridaben or a pyridaben analog attached to an imaging moiety, including a radioisotope for use in nuclear medicine imaging such as $^{18}$F.

Synthesis methods for the various radiopharmaceuticals described herein are known in the art and reference can be made to published applications WO 2011006610 and WO 2011097649, the entire contents of which are incorporated by reference herein.

The filtering step may be performed as follows:

A composition comprising the radiopharmaceutical is sterile filtered (e.g., using a Sartorius RC or Millipore PTFE sterilizing filter) into a sterile empty vial. The filter diameter is typically selected based on the manufacturer's standard for the actual volume of the composition to be filtered. Typically, a composition volume of 5 mL, up to 10 mL, up to 20 mL, up to 30 mL, up to 40 mL, up to 50 mL or greater may be filtered. In one embodiment, a filter with a diameter of 4 mm may be used to filter 5 mL of a composition comprising a radiopharmaceutical. In another embodiment, a filter with a diameter of 13 mm may be used to filter about 5 mL, or about 10 mL of the composition. In yet another embodiment, a filter with a diameter of 15 mm may be used to filter about 5 mL, or about 10 mL, or about 20 mL of a composition comprising the radiopharmaceutical. In another embodiment, a filter with a diameter of 25 mm may be used to filter about 5 mL, or about 10 mL, or about 20 mL, or about 30 mL, or about 40 mL, or about 50 mL, or about 100 mL of the composition. The Sartorius RC filter is commercially available in 4, 15, and 25 mm diameters. The Millipore PTFE filter is commercially available in 13 and 25 mm diameters. The sterile empty vial used to receive the filtered composition may be a commercially available, pre-sterilized unit. Those of ordinary skill in the art would be able to select suitable sterile vials for filtration step.

As an example, a final product vial assembly may be constructed from the following pre-sterilized components: one 30 mL sterile empty vial, one Millipore Millex GV4 venting filter (0.22 μm×4 mm), one tuberculin syringe (1 mL) and one insulin syringe (0.5 mL). The imaging agent is then transferred from the formulation module of an automated radiopharmaceutical synthesis system (such as a GE TracerLab MX or Siemens Explora GN/LC module) to the final product vial assembly through a Sartorius RC sterilizing filter (0.2 μm×15 mm) or a Millipore PTFE sterilizing filter (0.2 μm×13 mm). Quality control samples are then removed, using the syringe assemblies, to complete all product release requirements.

In accordance with the invention, a variety of experiments were carried out to compare the properties of particular filters; Table 1 summarizes the relevant parameters for select filters evaluated herein. In general, the experiments involved filtering a composition comprising a fluorinated compound, as shown below and denoted as BMS-747158-01 in the accompanying Figures, and its hydroxylated congener, also shown below and denoted as BMS-747159-01 in the accompanying Figures.

In particular, compositions comprising BMS-747158-01 and BMS-747159-01 were prepared in water comprising absolute ethanol (4 wt. %) and sodium ascorbate (50 mg/mL; 5 wt. %) then loaded into plastic syringes (Norm-Ject™; 12 mL) and placed onto an automated syringe pump. Select filters were then placed on each respective syringe and the composition pumped through the units in a controlled fashion. In all cases, gravimetric analysis of the solution transfer process was performed in order to monitor efficiency of the liquid handling steps. Subsequent quantitative analysis of filter retention was then performed following HPLC determination of the absolute concentration of each analyte in both the pre- and post-filtered solutions; HPLC analysis with detection at 295 nm was performed according to established methods. The following equation was then utilized to determine the percent recovery for each analyte:

$$\% \text{ Recovery} = \frac{\text{final concentration}}{\text{initial concentration}} \times \frac{\text{volume collected}}{\text{volume transferred}} \times 100$$

Note a higher value of percent recovery equates to lower retention of the respective analyte, and thus improved overall filter performance. The analysis described herein captures both the mass of the compound that is retained as well as the volume of liquid that is retained. As no normalization is performed, the analysis thus allows for direct comparison of relevant filter parameters. Further, due to the differential magnitude in measured log D values for the individual analytes, the value of percent recovery for BMS-747159-01 serves as an internal control for the study; where due to its lower inherent lipophilicity, any mechanical problems associated with the filtration process manifest in reduced recovery of BMS-747159-01.

TABLE 1

Relevant filter parameters

| Source | Model | Size (mm) | Membrane | Coating | Housing |
|---|---|---|---|---|---|
| Millipore | Millix GV | 13 | PVDF | hydrophilic | HDPE |
| Millipore | Millix LG | 13 | PTFE | hydrophilic | HDPE |
| Pall | Acrodisc PVDF | 13 | PVDF | hydrophilic | PP |
| Pall | Acrodisc GHP | 13 | GHP | hydrophilic | PP |
| Pall | Acrodisc Nylon | 13 | Nylon | hydrophilic | PP |
| Pall | Acrodisc Teffryn | 13 | PS | hydrophilic | PP |
| Pall | Acrodisc SuPor | 13 | PES | hydrophilic | PP |
| Pall | Acrodisc MS | 25 | WWPTFE | hydrophilic | HDPE |
| Sartorius | Nylon 25 | 25 | Nylon | hydrophilic | PP |
| Sartorius | Minisart RC | 15 | cellulose | hydrophilic | PP |
| Sartorius | Minisart SRP | 25 | PTFE | hydrophobic | PP |

HDPE = High Density polyethylene
PP = Polypropylene
PTFE = polytetrafluorethylene
PVDF = polyvinylidene fluoride
PES = polyethersulfone
PS = polysulfone The compositions comprising BMS-747158-01 and BMS-747159-01 were passed through a variety of filters, as described herein. Individual filter parameters varied in terms of both membrane and housing composition, overall filter diameter, and in some instances the applied coating (Table 1). Further, effects of both individual analyte concentration as well as the overall rate of filtration were also evaluated.

Figure 1:
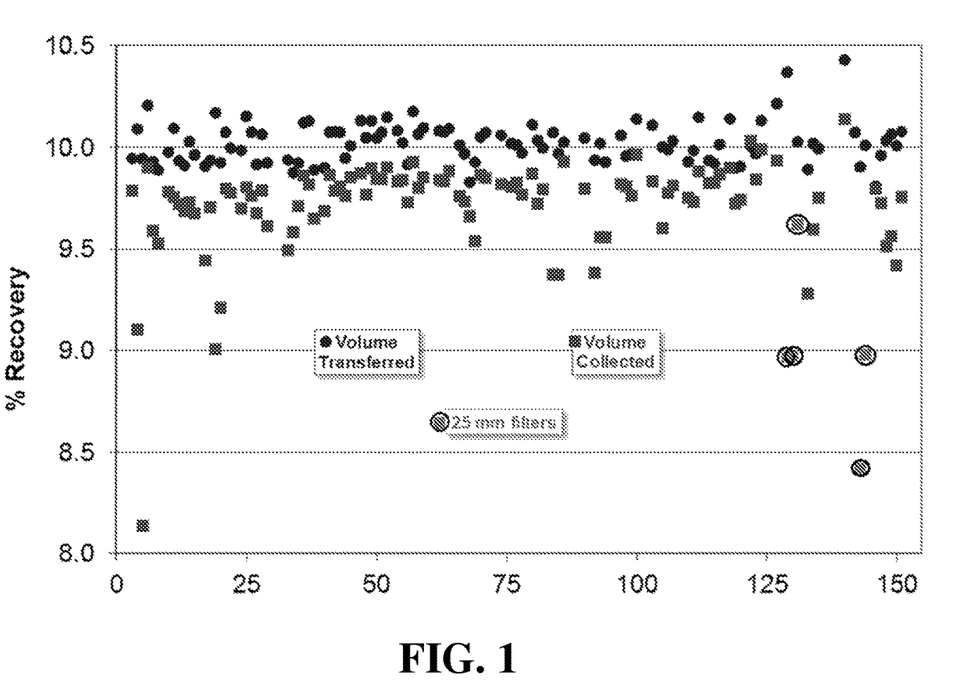
FIG. 1 is a graph showing liquid transfer efficiency through selected filters.

FIG. 1 demonstrates the liquid transfer efficiency of the process. Specifically, when the same diameter filter is utilized, the relationship between the volume and volume collected remains relatively consistent. When larger filters are used (without a concomitant increase in the volume of test solution), a difference is seen. The Figure therefore establishes that for a given filter diameter, near complete transfer of the test composition through the filter occurs.

Figure 2:
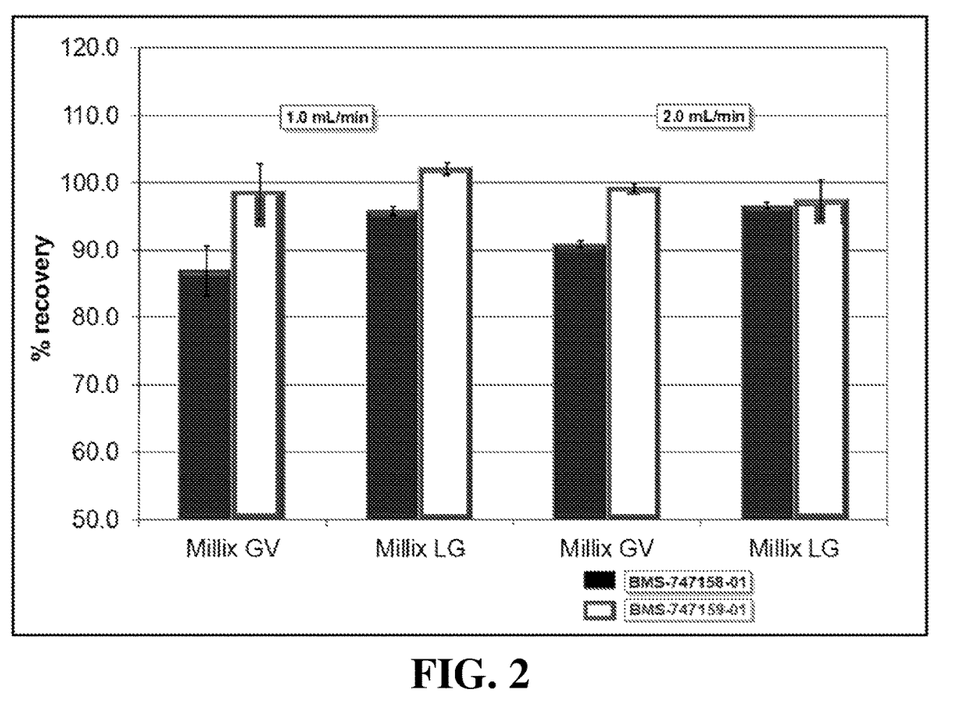
FIG. 2 is a bar graph showing dependence of individual analyte retention on overall filtration rate.

FIG. 2 demonstrates the effect of filtration rate on individual analyte recovery. Specifically, increased overall filtration rate did not appreciably change the recovery profiles of either analyte.

Figure 3:
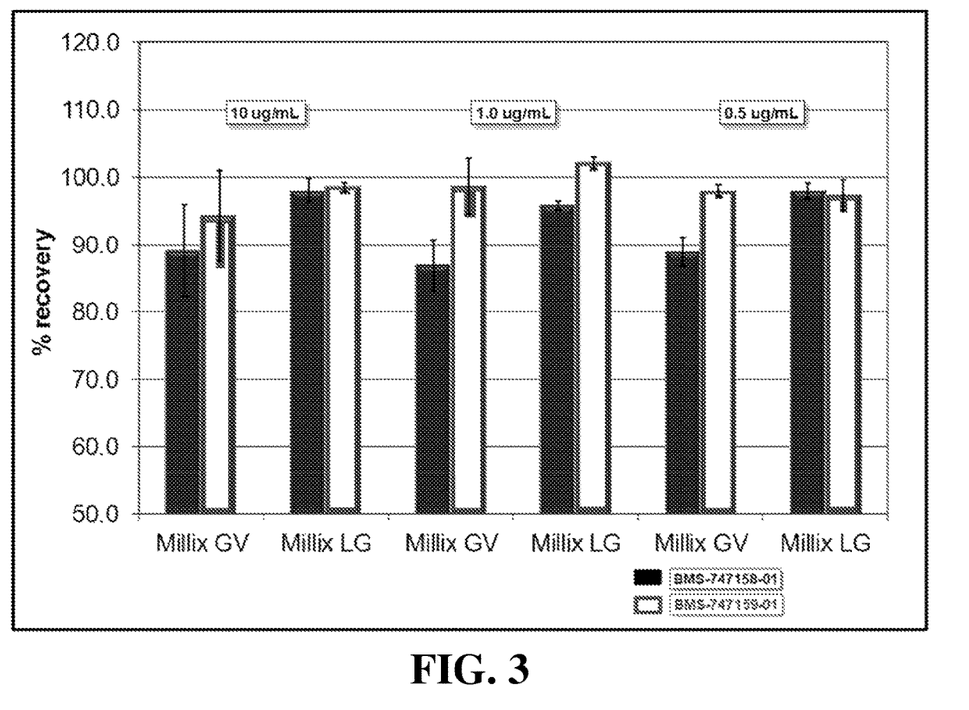
FIG. 3 is a bar graph showing dependence of individual analyte retention on overall solution concentration.

FIG. 3 demonstrates the effect of increasing analyte concentration on individual analyte recovery. Specifically, the data demonstrate that the filters were not saturated when solutions comprising 10 µg/mL, 1 µg/mL, or 0.5 µg/mL of the individual analytes were employed; the recovery profiles for a given filter did not change appreciably between these various concentrations.

Figure 4:
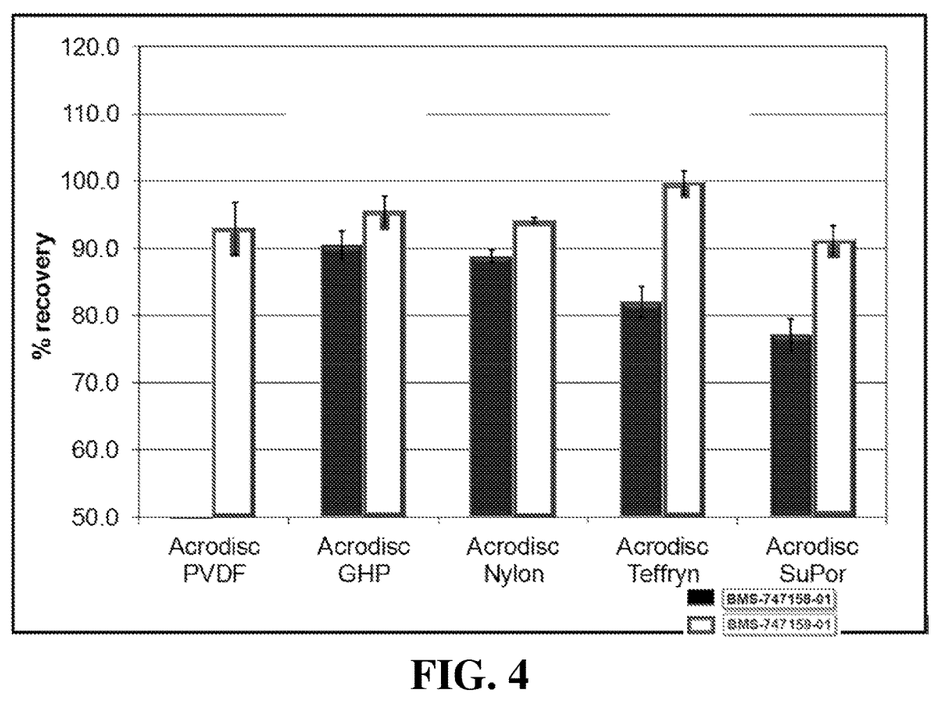
FIG. 4 is a bar graph showing dependence of individual analyte retention on filter membrane composition.

FIG. 4 demonstrates the effect of membrane composition on individual analyte recovery. Given filters of identical diameter, differential recovery of BMS-747158-01 is observed for a given membrane composition. Unexpectedly, the PVDF membrane retains the greatest amount of BMS-747158-01.

Figure 5:
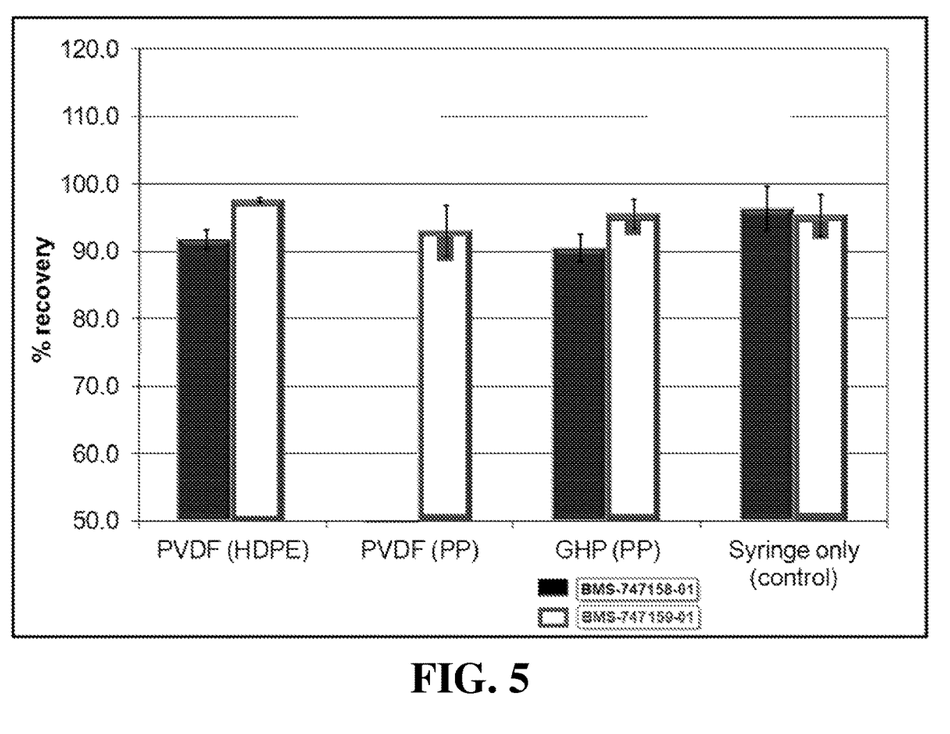
FIG. 5 is a bar graph showing dependence of individual analyte retention on filter membrane and housing composition.

FIG. 5 demonstrates the effect of filter membrane and housing composition on individual analyte recovery. Given filters of identical diameter, it was found in accordance with the invention that filter housings comprising materials that lacked aromatic rings such as high density polyethylene (HDPE) and polypropylene (PP) retained lower amounts of BMS-747158-01. In contrast, filter housings comprising aromatic rings, such as polystyrene and polyacrylates, are less suitable.

Figure 6:
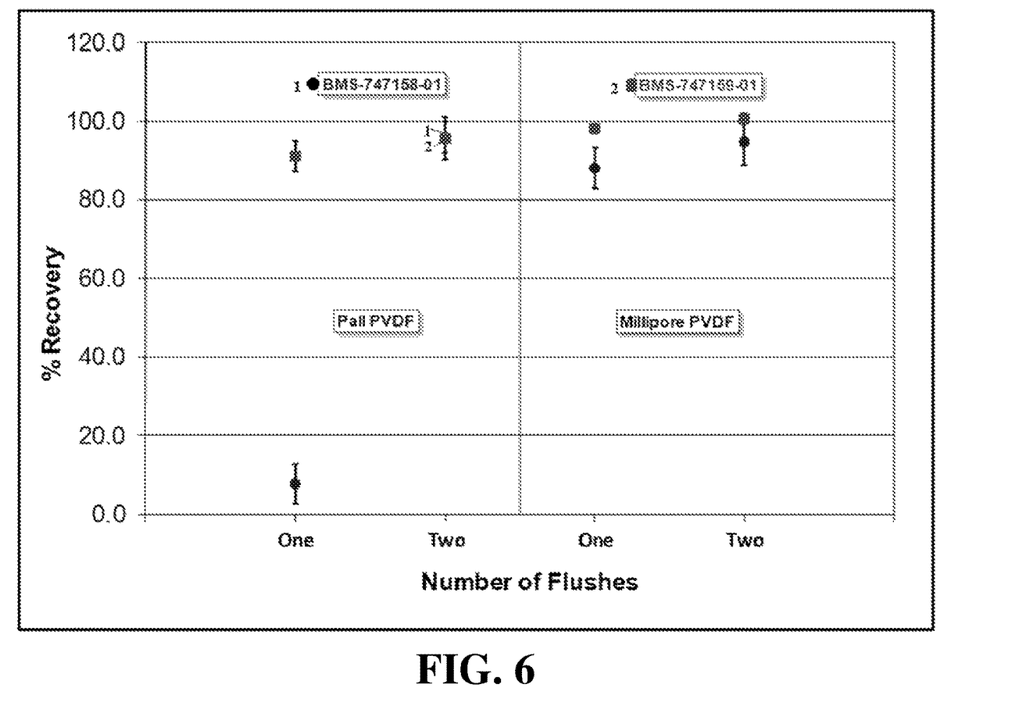
FIG. 6 is a graph showing the results of a flushing study.

FIG. 6 demonstrates that certain filters have high levels of non-specific binding. An example of such a filter is the Pall PVDF filter, which retained large amounts of BMS-747158-01 (but not BMS-747159-01) after the initial filtration. Interestingly, the same filter yielded nearly 100% recovery of BMS-747158-01 following a second filtration of the solution matrix itself (10 mL), indicating that non-specific binding occurred during initial filtration of the analyte composition.

Figure 7:
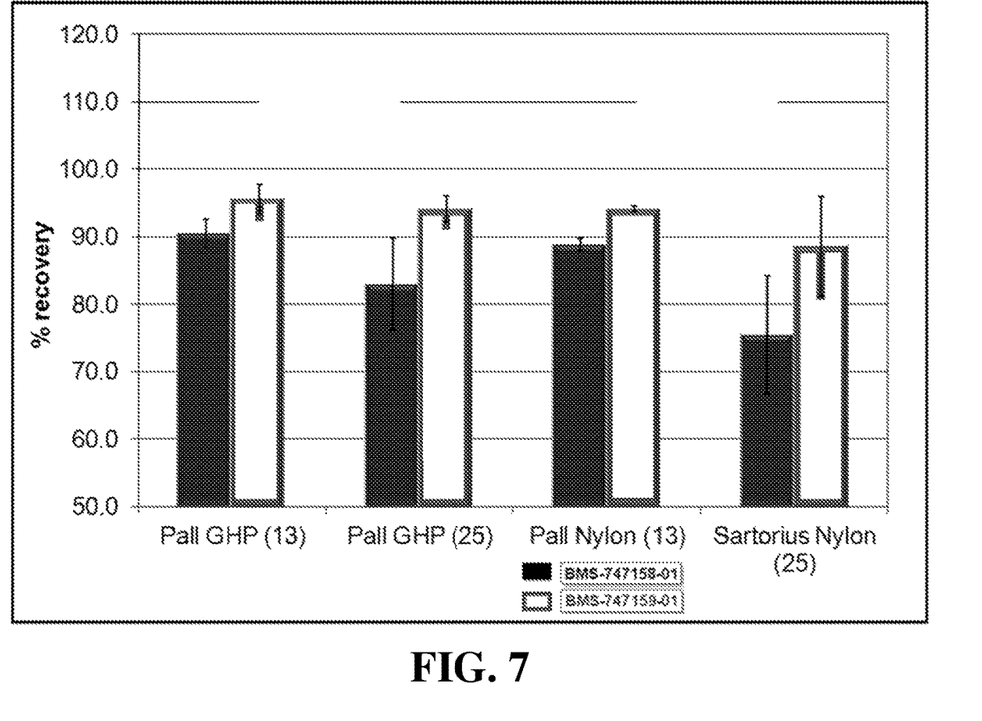
FIG. 7 is a bar graph showing dependence of individual analyte retention on filter size and membrane composition.

FIG. 7 demonstrates the effect of increasing filter diameter (or surface area) on individual analyte recovery. Specifically, the data demonstrate that larger filter diameters retain greater amounts of BMS-747158-01. The high recovery values for BMS-747159-01 indicate that mechanical retention of the solution (increased filter dead volume) did not occur. Note the numbers in parentheses indicate the filter diameter values.

Figure 8:
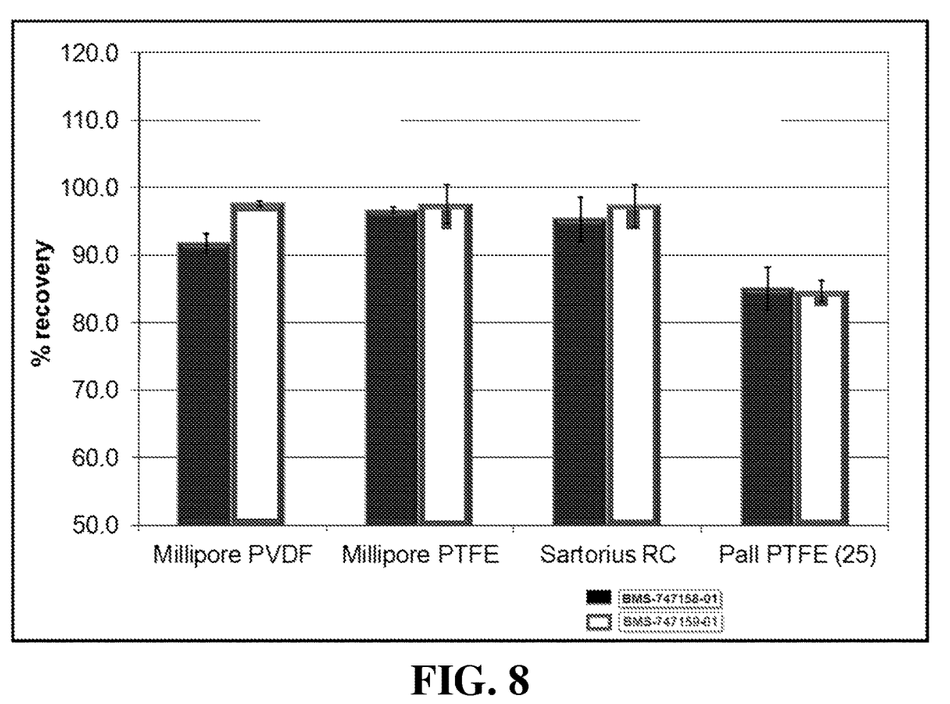
FIG. 8 is a bar graph showing a comparison of select filters.

FIG. 8 provides a direct comparison of selected filters. Specifically, the data indicate that PTFE and RC filter membranes retained lower amounts of BMS-747158-01 in comparison to the PVDF congener. The equivalent, yet lower percent recovery of BMS-747158-01 and BMS-747159-01 observed when using the 25 mm PTFE filter, however indicate that mechanical retention of the analyte composition may occur when utilizing filters with larger housing diameters.

Figure 9:
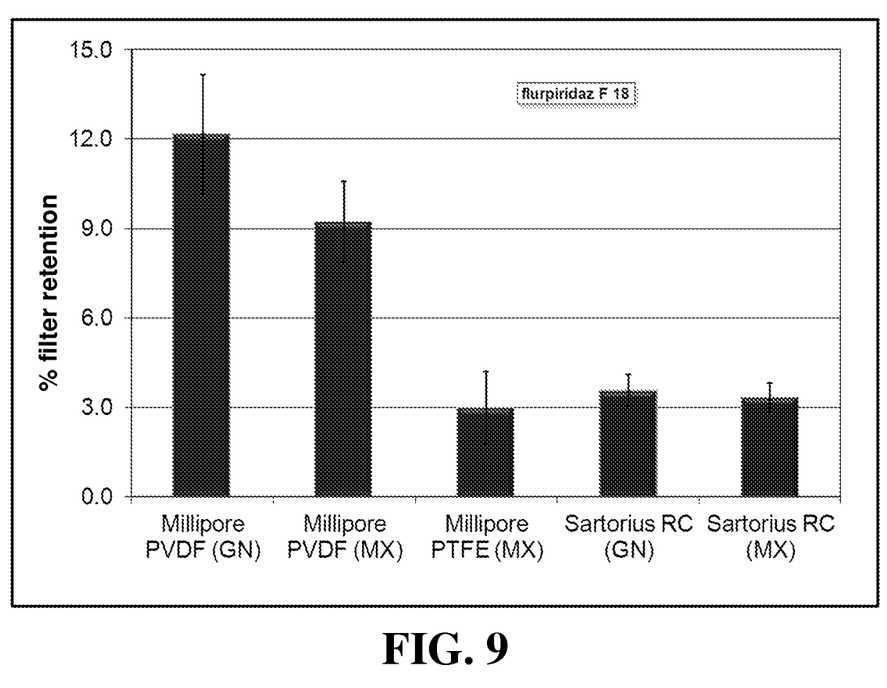
FIG. 9 is a bar graph showing dependence of flurpiridaz F 18 retention on selected filters and synthesis modules.

FIG. 9 demonstrates the retention profile of the PVDF, PTFE and RC filter membranes for the $^{18}$F-bearing radiopharmaceutical, flurpiridaz F 18 and the effect of manual vs. automated filtration techniques utilized with the Siemens Explora GN/LC and GE TracerLab MX modules, respectively. Clearly the PTFE and RC filters retain far less of the radiopharmaceutical than does the PVDF filter. This was particularly surprising since structurally and chemically, the PVDF filter is more similar to the PTFE filter than the RC filter. Further, the data substantiate that use of the RC filter membrane improves recovery of $^{18}$F-bearing radiopharmaceuticals across multiple synthesis module platforms.

These experiments demonstrate the superiority of the PTFE and RC filters for $^{18}$F-bearing radiopharmaceuticals such as flurpiridaz F 18.

All patent applications and patents recited herein are incorporated by reference herein in their entirety unless otherwise stated. In case of conflict, the present specification, including definitions, controls.

The invention claimed is:
1. A method comprising
   passing a composition comprising an $^{18}$F-bearing radiopharmaceutical through a hydrophilic regenerated cel- lulose filter to achieve a filtered composition, wherein recovery of the $^{18}$F-bearing radiopharmaceutical after passage through the filter is greater than about 90%, wherein the $^{18}$F-bearing radiopharmaceutical is:

flurpiridaz F 18

2. The method of claim 1, wherein the composition comprises ascorbic acid.

3. The method of claim 2, wherein the concentration of ascorbic acid is about 50 mg/mL.

4. The method of claim 1, wherein the composition has a pH of about 5.8.

5. The method of claim 1, wherein the composition further comprises about 50 mg/mL ascorbic acid and has a pH of about 5.8.

6. The method of claim 1, wherein recovery of the $^{18}$F-bearing radiopharmaceutical after passage through the filter is greater than 95%.

7. A method comprising
passing a composition comprising an $^{18}$F-bearing radiopharmaceutical through a hydrophilic regenerated cellulose filter to achieve a filtered composition, wherein retention of the $^{18}$F-bearing radiopharmaceutical after passage through the filter is less than 5% wherein the $^{18}$F-bearing radiopharmaceutical is:

flurpiridaz F 18

8. The method of claim 7, wherein the composition comprises ascorbic acid.

9. The method of claim 8, wherein the concentration of ascorbic acid is about 50 mg/mL.

10. The method of claim 7, wherein the composition has a pH of about 5.8.

11. The method of claim 7, wherein the composition further comprises about 50 mg/mL ascorbic acid and has a pH of about 5.8.

12. The method of claim 7, wherein retention of the $^{18}$F-bearing radiopharmaceutical after passage through the filter is less than 4%.

13. The method of claim 7, wherein retention of the $^{18}$F-bearing radiopharmaceutical after passage through the filter is less than 3%.

14. The method of claim 1, wherein the composition comprising the $^{18}$F-bearing radiopharmaceutical is a composition of the $^{18}$F-bearing radiopharmaceutical in an aqueous solution comprising 3-5 wt % ethanol.

15. The method of claim 7, wherein the composition comprising the $^{18}$F-bearing radiopharmaceutical is a composition of the $^{18}$F-bearing radiopharmaceutical in an aqueous solution comprising 3-5 wt % ethanol.

* * * * *